United States Patent [19]

Spann

[11] 3,939,829

[45] Feb. 24, 1976

[54] RESTRAINING CUFF

[76] Inventor: Donald C. Spann, 5 Ferncreek Court, Greenville, S.C. 29607

[22] Filed: July 9, 1974

[21] Appl. No.: 486,763

[52] U.S. Cl. ............................. 128/133; 128/80 R
[51] Int. Cl.² ........................................... A61F 5/37
[58] Field of Search.......... 128/133, 134, 149, 80 R, 128/80 A–J, 80 DB, 111, 87 R, 89 R; 5/338

[56] References Cited
UNITED STATES PATENTS

| | | | |
|---|---|---|---|
| 2,998,008 | 8/1961 | Klesa ................................. | 128/133 |
| 3,297,026 | 1/1967 | Van Pelt............................. | 128/133 |
| 3,505,994 | 4/1970 | Smith, Jr........................... | 128/80 R |
| 3,713,437 | 1/1973 | Wiedmer........................... | 128/80 E |

Primary Examiner—Robert W. Michell
Assistant Examiner—Henry J. Recla
Attorney, Agent, or Firm—Bailey & Dority

[57] ABSTRACT

A restraining cuff and the like is formed from a block of polyurethane foam having resilient characteristics, capable of permitting the passage of air and being of such configuration as to include a continuous substantially cylindrical internal wall extending longitudinally of the block for receiving the extremities of a hospitalized patient so as to provide a closed circumferential layer of resilient deformable material which may be connected as by a flat strap to the patient so as to distribute the weight of the extremity upon a substantial area of foam and cushion against bruises and other forms of injury to the patient.

2 Claims, 6 Drawing Figures

U.S. Patent    Feb. 24, 1976    Sheet 1 of 2    3,939,829
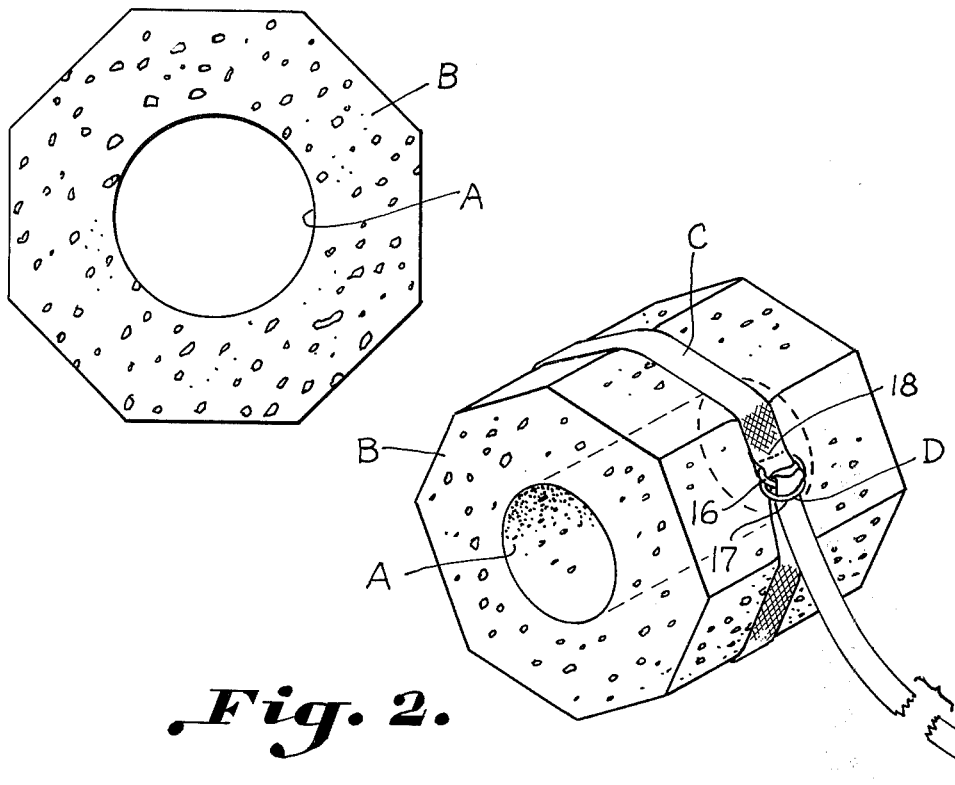
Fig. 1.
Fig. 2.
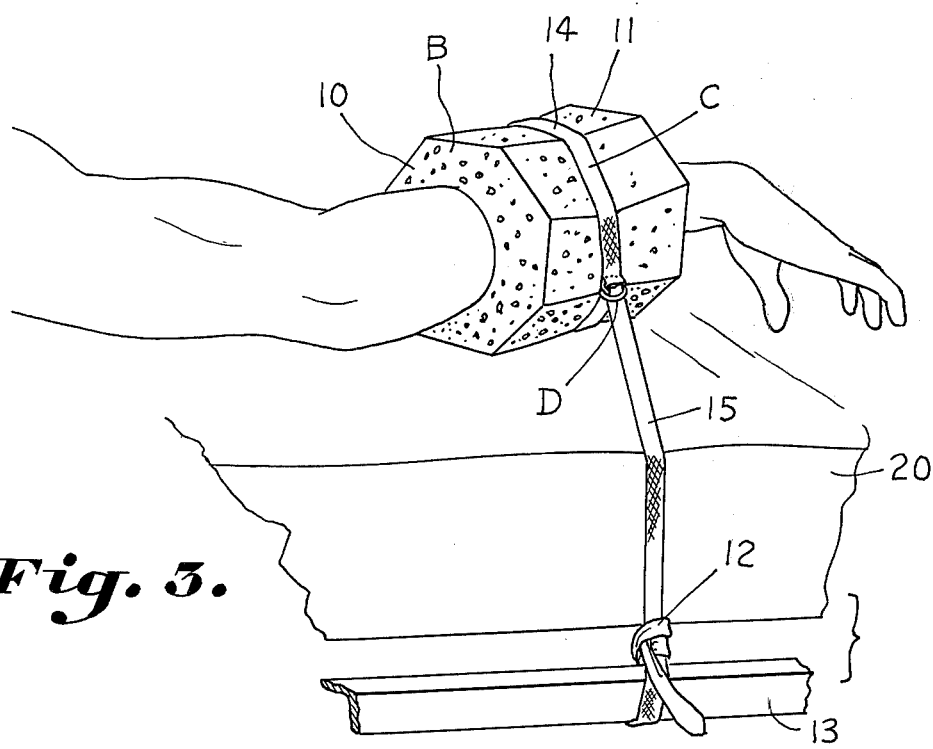
Fig. 3.

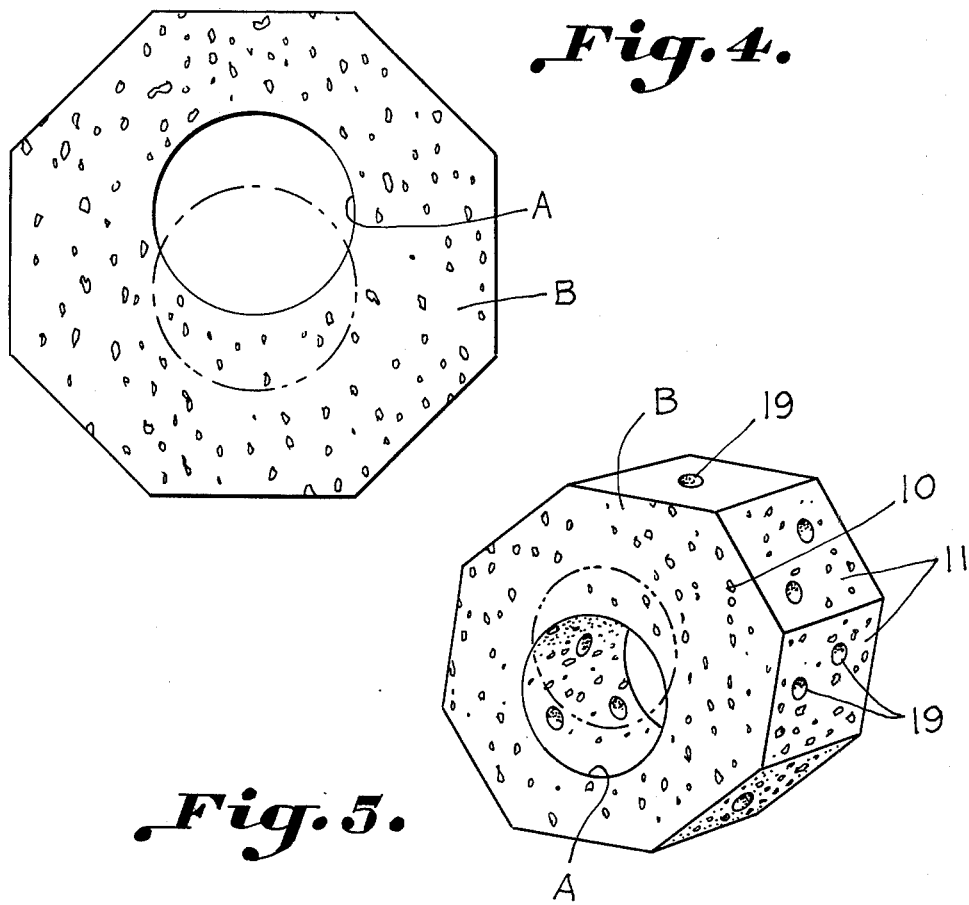
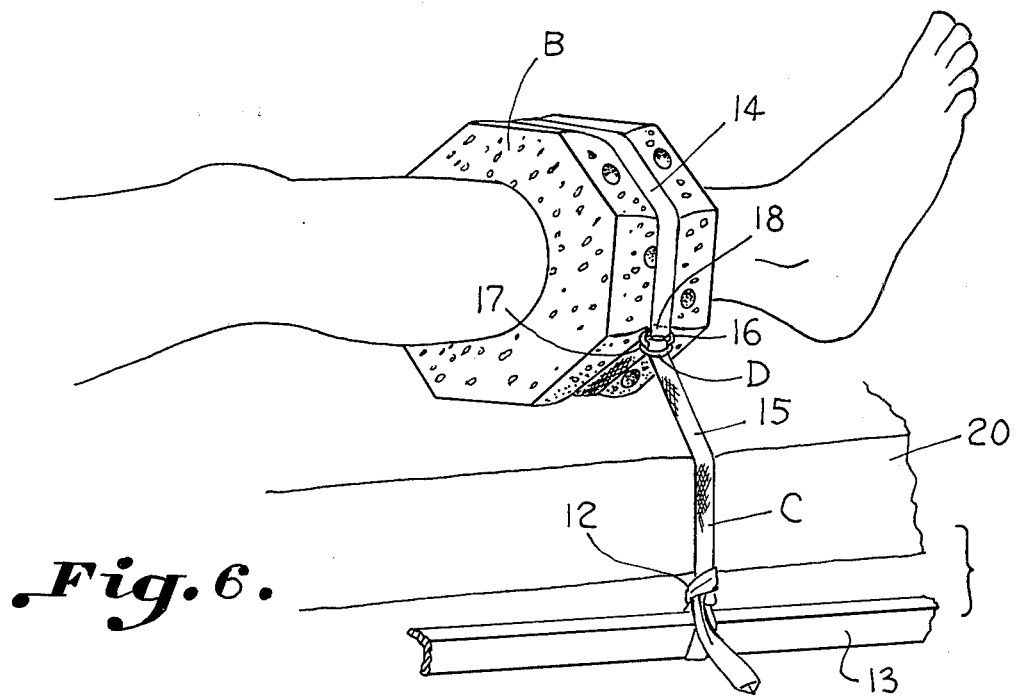

RESTRAINING CUFF

BACKGROUND OF THE INVENTION

Heretofore, leather straps and the like have been employed to restrain the limbs of hospitalized patients against thrashing around as after surgery has been performed. Such straps and the like tend to produce raw skin on the patient since engagement is confined to a relatively small area of the skin. Injury can be caused as a result of movement permitting the hand or foot to strike the sides of the bed. A jerking of the arm, for example, would remove tubes and the like from the arm of the patient. Other such devices utilize relatively thin foam strips with straps attached thereto in an effort to avoid chaffing. Such devices are relatively expensive and are maintained as a permanent part of the hospital's equipment.

In the case of a patient's feet prolonged bed rest often results in the formation of ulcers on the heel as a result of the concentration of weight on the heel bearing against the mattress. Prior art devices include the use of a large boot generally constructed of polyvinyl chloride with a polyethylene foam liner. Such devices have been found not to prevent ulcers because the weight is still concentrated at the heel.

Accordingly, it is an important object of the present invention to provide a restraining cuff and the like for use on the arms generally adjacent the wrist and forearm and on the ankles and lower calf of patients who are either confined to prolonged bed rest or those who tend to thrash around as would be the case with a patient in the recovery room after an operation.

A further object of the invention is to provide such a restraining member which is constructed of resilient material which will permit air flow around the limb and spread the area of engagement with the skin to avoid raw skin and chaffing of the limbs so as to prevent unwanted movement of the limb and afford a good grip of a limb area.

Another important object of the invention is to provide such a device which will cushion the limb since an extensive area of thick foam material is provided entirely about the limb to avoid bruises. The device is comfortable and is especially useful with old people whose bones are brittle and require prolonged care.

Still another object of the invention is to provide comfortable restraining devices which may be inexpensively produced so that use may be confined to one patient and which elevates the extremity to avoid prolonged contact with the mattress.

SUMMARY OF THE INVENTION

It has been found that a restraining member may be constructed of a resilient, deformable polyurethane foam block so as to provide a central opening for reception of the extremity of a hospital patient affording a thick continuous circumferential layer of material which will provide a good grip over a large area of the extremity permitting elevation of the extremity to avoid prolonged contact with the mattress and facilitate restraint of the extremity by permitting easy fastening to a bed frame or the like.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein:

FIG. 1 is a front elevation illustrating a restraining cuff constructed in accordance with the present invention, FIG. 2 is a perspective view further illustrating the restraining cuff, FIG. 3 is a perspective view illustrating the restraining cuff of FIGS. 1 and 2 carried upon the wrist and forearm of a patient for restraining the limb against undesired movement, FIG. 4 is a front elevation of a restraining cuff constructed in accordance with a modified form of the invention, FIG. 5 is a perspective view further illustrating the modified form of the invention, and FIG. 6 is a perspecctive view illustrating the modified form of the invention positioned upon the ankle and lower calf of a patient restraining the limb against undesired movement.

DESCRIPTION OF A PREFERRED EMBODIMENT

The drawings illustrate a restraining cuff and the like for placement upon the extremities of a patient confined to prolonged bed rest, and for restraining undesired movement of a patient reclining upon a bed.

An elongated block of resilient deformable polyurethane foam material has a substantially cylindrical internal wall A extending longitudinally of the elongated block defining a thickened closed circumferential layer B of resilient deformable material capable of maintaining an extremity placed within the wall in elevated position above a mattres of the bed. A strap C encircles a medial outer portion of the block and extends free of the block providing a tie portion for fastening to the bed. Adjustable fastening means D secures the strap encircling the block constricting said circumferential layer of foam resiliently engaging an extremity of a patient. Thus, chaffing of the extremity engaged by the cuff is avoided as well as prolonged contact between the extremity and the mattress. The structure is especially adapted for receiving the ankle and lower calf as the internal wall is positioned longitudinally eccentrically of the block so that the block may be positioned on the extremity to position same at a selected height above the mattress.

Referring especially to FIGS. 1, 2 and 3, it will be noted that the elongated block of resilient deformable polyurethane foam has been formed as by cutting or sawing a block to provide a front face 10 and a plurality of flat side faces 11. It has been found that the outer surface of the block is most advantageously formed into a series of flat surfaces 11 to facilitate manufacture and use. It will be noted be referring to FIG. 3 that the restraining cuff may be tied as by a knot 12 to the frame 13 of a hospital bed. A strap portion 14 encircles a medial portion of the outer periphery of the block and is secured by the fastening means accommodating a free extending portion 15 which is of sufficient length to permit the tying of the knot 12.

The fastening means D preferably includes a buckle of the type employing a pair of rings 16 and 17 which are fastened to one end of the back portion 14 as by stitching illustrated at 18. The strap may be fastened by passing the free hand through both rings and then passing same over the upper ring 16 and thence beneath the lower ring 17. The strap may be pulled to the desired tightness and it will maintain the foam layer in a constricted relation about the arm or leg to provide protection against release of the limb as well as unwanted movement of the limb. It will be observed that the thickened, closed circumferential layer B may be provided with a series of circumferentially and randomly spaced holes 19 extending radially through the thickened layer. Thus, air flow is further promoted about the limb as a result of pumping action which occurs as a result of compression and decompression of the foam as results from any force tending to move the limb. It will be further noted from referring to FIG. 3 that the arm is held in somewhat elevated position above the mattress tending to spread the weight of the limb over a substantial area of the foam minimizing contact between the limb and the mattress 20.

Refferring now especially to FIGS. 4, 5 and 6 wherein like reference characters are used to designate like parts, it will be noted that the internal wall is eccentrically positioned longitudinally of the block rather than on a central axis as in the restraining device illustrated in FIGS. 1, 2 and 3. The transverse openings 19 may, of course, be used in any embodiment of the invention. By positioning the cylindrical internal wall A eccentrically of the block, the block may be turned upon the extremity as in the case of FIG. 6 to place the major thickness of the block in contact with the mattress permitting substantial elevation of the extremity in the area of contact by the restraining device in a substantially elevated position to minimize contact of the extremity with the mattress spreading the area of contact of the limb with the mattress, especially minimizing contact of the heel of the patient reducing the tendency to cause ulcers as often occurs on the heel of those confined to extended periods of bed rest. The eccentric opening may also be utilized upon arm supporting versions of the device of the invention. If desired, as in the case of a woman, child or small patient, a minimum thickness of the circumferential layer may be placed in engagement with the mattress by turning the block upon the limb so as to provide such adjustment. The block may assume any such positions so as to vary the height of the limb between the maximum and minimum heights resulting from the positioning of the block set forth above.

While a preferred embodiment of the invention has been described using specific terms, such description is for illustrative purposes only, and it is to be understood that changes and variations may be made without departing from the spirit or scope of the following claims.

What is claimed is:

1. A restraining cuff and the like comprising:
   restraining means for placement upon the extremities of a patient confined to prolonged bed rest for elevating the extremities, and for restraining undesireable movement of a patient reclining upon a bed;
   said restraining means including,
      an elongated block of resilient deformable polyurethane foam material;
      said elongated block including a bore therethrough defining a continuous internal wall extending longitudinally of said elongated block for receiving an extremity:
   said restraining means further defining a thickened, closed integral circumferential cylindrical layer of resilient deformable material, wherein the distance in cross section from said internal wall to the perimeter of said layer maintains an extremity placed within said wall in elevated position above a mattress of the bed so as to avoid pressure point contact between the extremity and the mattress as would result in the formation of decubitus ulcers;
   a strap encircling a medial outer portion of said block and extending free of said block providing a tie portion for fastening to the bed; and
   adjustable fastening means for securing said strap encircling the block constricting said circumferential layer of foam resiliently engaging an extremity of a patient;
   whereby chaffing of the extremity engaged by the cuff may be avoided and the extent of contact between the extremity and the mattress reduced.

2. The structure set forth in claim 1 wherein said internal wall is positioned longitudinally eccentrically of said block, whereby the block may be positioned on the extremity to position same at a selected height above the mattress.

* * * * *